US009567283B2

(12) United States Patent
Garel et al.

(10) Patent No.: US 9,567,283 B2
(45) Date of Patent: Feb. 14, 2017

(54) METHOD FOR SEPARATING MANDELIC COMPOUNDS IN SALIFIED FORM AND USE OF SAME FOR PREPARING AROMATIC ALDEHYDE

(71) Applicant: RHODIA OPERATIONS, Paris (FR)

(72) Inventors: Laurent Garel, Lyons (FR); Stephanie Normand, Saint-Genis-Laval (FR); Stephanie Foucher, Shanghai (CN); Dominique Horbez, Franconville (FR); Morad Assam, Chambost-Longessaigne (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 15/105,047

(22) PCT Filed: Dec. 15, 2014

(86) PCT No.: PCT/EP2014/077701
§ 371 (c)(1),
(2) Date: Jun. 16, 2016

(87) PCT Pub. No.: WO2015/091328
PCT Pub. Date: Jun. 25, 2015

(65) Prior Publication Data
US 2016/0318839 A1   Nov. 3, 2016

(30) Foreign Application Priority Data

Dec. 18, 2013 (FR) ..................................... 13 02986

(51) Int. Cl.
| C07C 51/47 | (2006.01) |
| B01D 15/08 | (2006.01) |
| C07C 51/41 | (2006.01) |
| C07C 45/29 | (2006.01) |
| C07C 45/61 | (2006.01) |

(52) U.S. Cl.
CPC ............... *C07C 51/47* (2013.01); *B01D 15/08* (2013.01); *C07C 45/29* (2013.01); *C07C 45/61* (2013.01); *C07C 51/41* (2013.01)

(58) Field of Classification Search
None
See application file for complete search history.

(56) References Cited

U.S. PATENT DOCUMENTS

| 6,753,441 B1 | 6/2004 | Jouve et al. |
| 2011/0230674 A1 | 9/2011 | Desouhant-Massacret |
| 2012/0103786 A1 | 5/2012 | Gayet et al. |
| 2012/0264982 A1 | 10/2012 | Desouhant-Massacret |
| 2015/0034551 A1 | 2/2015 | Garel et al. |

FOREIGN PATENT DOCUMENTS

| WO | 9965853 A1 | 12/1999 |
| WO | 2009141280 A1 | 11/2009 |
| WO | 2010007161 A1 | 1/2010 |
| WO | 2011039331 A1 | 4/2011 |
| WO | 2013135885 A1 | 9/2013 |

*Primary Examiner* — Sudhakar Katakam
*Assistant Examiner* — Jennifer C Sawyer

(57) ABSTRACT

The invention describes a method for separating a mandelic compound in salified form from an aqueous reaction medium resulting from the condensation reaction of a hydroxylated aromatic compound with glyoxylic acid in a basic medium, said method comprising a) decanting said reaction medium in such a way as to recover an organic phase formed from the excess of said aromatic compound and an aqueous phase formed from said mandelic compound and a quantity of the excess of said aromatic compound and b) bringing said aqueous phase into contact with an adsorbent support, resulting in the selective adsorption of said aromatic compound and the recovery of an aqueous flow comprising said mandelic compound in salified form, which is subjected to an oxidation step before being converted into hydroxyaromatic aldehyde by electrodialysis.

21 Claims, No Drawings

METHOD FOR SEPARATING MANDELIC COMPOUNDS IN SALIFIED FORM AND USE OF SAME FOR PREPARING AROMATIC ALDEHYDE

This application is a U.S. national stage entry under 35 U.S.C. §371 of International Patent Application No. PCT/EP2014/077701, filed Dec. 15, 2014, which claims priority to French Application No. 1302986, filed on Dec. 18, 2013, the whole content of each of these applications is hereby incorporated herein by reference for all purposes.

The present invention relates to the field of separating mandelic aromatic compound(s) and of preparing aromatic aldehyde(s) from said mandelic aromatic compound(s).

In the description that follows of the invention, the mandelic group means the —CHOH—COOH group, which is present as a substituent on the aromatic nucleus of said mandelic aromatic compound(s).

The present invention is more particularly directed toward the preparation of the acid 4-hydroxy-3-methoxybenzaldehyde, also known as vanillin, from a salt of 4-hydroxy-3-methoxymandelic acid and the preparation of the acid 3-ethoxy-4-hydroxybenzaldehyde, also known as ethylvanillin, from a salt of 3-ethoxy-4-hydroxymandelic acid.

Vanillin is obtained from natural sources, such as lignin or ferulic acid, but a substantial proportion of vanillin is produced via the chemical route. Numerous diverse and varied preparation methods are described in the literature (Kirk-Othmer-Encyclopedia of Chemical Technology, 24, pages 812-825, 4th edition (1997)). A conventional route of access to vanillin involves a condensation reaction of glyoxylic acid with guaiacol in basic medium to obtain 4-hydroxy-3-methoxymandelic acid. Guaiacol is extracted from its reaction medium before being subjected to an oxidation step. Vanillin is then obtained after neutralization of the vanillate salt obtained on conclusion of said oxidation step and subsequent extraction of the vanillin. This conventional process, although efficient, has the drawbacks of high energy consumption, in the form of steam, of generating large amounts of saline effluents and of high consumption of base, generally sodium hydroxide, and of strong mineral acid, generally sulfuric acid. To reduce both the amounts of salts generated and the amounts of base and of strong acid, a first improvement was made by recovering the mandelic acid salts, on conclusion of the condensation reaction, by selective adsorption of the excess guaiacol (WO 2011/039331). However, this improvement suffers from the need to perform the adsorption step with a high concentration of guaiacol in the stream to be separated and consequently of requiring a sizeable adsorption device. The need to relieve the adsorption device in order to further space out the regeneration phases and to treat a smaller amount of stream to be separated is great, and the object of the present invention is to overcome the drawbacks encountered during the recovery of the mandelic acid salts by simple adsorption. Another object of the present invention is to improve the competitiveness of the process for preparing aromatic aldehyde, especially vanillin and ethylvanillin, by seeking to reduce even further the amount of salts generated during the various neutralization steps. This object is achieved by implementing an alternative technique for acidifying the basic aqueous stream derived from the oxidation step, said stream being acidified by using the electrodialysis technique, which does not require the input of an external acid source. This results in a drastic reduction in the generation of salts, particularly sulfate salts, in one section of the process which up until now leads to a large production of salts.

The result of implementing the process of the invention, combining both the separation of mandelic acid salts by selective adsorption preceded by a step of decantation and neutralization of the basic oxidation stream by electrodialysis, is a considerable reduction in the salts produced relative to the amount produced by performing the current process. An at least 85% reduction in the salts produced, preferably at least 90% or even at least 98%, was achieved with the aromatic aldehyde preparation process according to the invention.

The subject of the present invention is, first, a process for separating at least one mandelic compound in salified form from an aqueous reaction medium resulting from the condensation reaction, in water, of at least one aromatic compound bearing at least one hydroxyl group and in which the para position is free with glyoxylic acid in basic medium, said process comprising at least the following steps:
  a) decantation of said reaction medium so as to recover an organic phase essentially comprising the excess of said aromatic compound and an aqueous phase formed from at least said mandelic compound and an amount of the excess of said aromatic compound,
  b) placing said aqueous phase in contact with an adsorbent support, leading to selective adsorption of said aromatic compound on said support and to the recovery of an aqueous stream comprising at least said mandelic compound in salified form.

In the description that follows, the term "aromatic compound" means a cyclic compound bearing delocalized double bonds as defined in the literature, especially by M. Smith and J. March, *Organic Chemistry*, 5th edition, John Wiley & Sons, 1992, pages 46 et seq.

The separation process according to the invention applies most particularly to an aromatic compound such as phenol, but also to substituted phenols having at least one unsubstituted position para to the hydroxyl group. The aromatic nucleus bears at least one hydroxyl group, but it may also bear one or more other substituents. Generally, the term "several substituents" defines less than four substituents per aromatic nucleus. Any substituent may be present insofar as it does not interfere in the condensation reaction. According to the invention, said aromatic compound bearing at least one hydroxyl group is also known as a "hydroxylated aromatic compound".

Thus, the separation process according to the invention is suitable for being applied to hydroxylated aromatic compounds corresponding to formula (I) below:

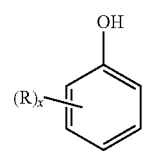

(I)

in said formula:
  at least the position para to the hydroxyl group is free,
  R represents a hydrogen atom or one or more identical or different substituents,
  x, the number of substituents on a ring, is a number less than or equal to 4.
  In formula (I), the groups R, which may be identical or different, represent a hydrogen atom, an alkyl, alkenyl, alkoxy, hydroxyalkyl, alkoxyalkyl, cycloalkyl, aryl or arylalkyl group, a hydroxyl group, a nitro group, a halogen atom, a halo or perhaloalkyl group, a formyl group, an acyl group containing from 2 to 6 carbon atoms, a carboxylic group, or an amino or amido group optionally substituted with one or two alkyl or phenyl groups. It should be noted that the carboxylic group may be salified, preferably with an alkali metal (sodium or potassium), or esterified, for example with an alkyl or phenyl group.

In formula (I), when x is greater than 1, two groups R placed on two vicinal carbon atoms may be linked together via an alkylene, alkenylene or alkenylidene group containing from 3 to 5 carbon atoms to form a saturated, unsaturated or aromatic ring containing from 5 to 7 atoms, it being possible for one or more (preferably 2 or 3) carbon atoms to be replaced with a heteroatom, preferably oxygen.

Within the context of the invention, the term "alkyl" means a linear or branched saturated hydrocarbon-based chain containing from 1 to 15 carbon atoms and preferably 1 or 2 to 10 carbon atoms.

The term "alkoxy" means a group alkyl-O— in which the term "alkyl" has the meaning given above. Preferred examples of alkoxy groups are methoxy or ethoxy groups.

The term "alkenyl" means a linear or branched hydrocarbon-based group containing from 2 to 15 carbon atoms, comprising one or more double bonds, preferably from 1 to 2 double bonds.

The term "cycloalkyl" means a cyclic hydrocarbon-based group comprising from 3 to 8 carbon atoms, preferably a cyclopentyl or cyclohexyl group.

The term "aryl" means a mono- or polycyclic, preferably mono- or bicyclic, aromatic group comprising from 6 to 12 carbon atoms, preferably phenyl or naphthyl.

The term "arylalkyl" means a linear or branched hydrocarbon-based group bearing a monocyclic aromatic ring and comprising from 7 to 12 carbon atoms, preferably benzyl.

The term "halo- or perhaloalkyl" means one of the following groups:
—$CX_3$, —$[CX_2]_p$—$CX_3$ or —$C_pH_aF_b$; in said groups, X represents a halogen atom, preferably a chlorine or fluorine atom, p represents a number ranging from 1 to 10, b a number ranging from 3 to 21 and a+b=2p+1.

In the case where x is greater than 1, two groups R placed on two vicinal carbon atoms may be linked together via an alkylene, alkenylene or alkenylidene group to form a saturated, unsaturated or aromatic ring containing from 5 to 7 atoms, thus forming a bicycle. Examples of preferred bicyclic backbones are as follows:

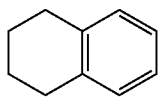 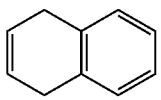 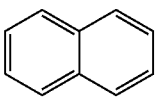

The compounds that are particularly suitable for use in the separation process of the invention correspond to formula (I) in which R, which may be identical or different, represent:
 a hydrogen atom,
 a hydroxyl group,
 a linear or branched alkyl group containing from 1 to 6 carbon atoms and preferably from 1 to 4 carbon atoms, such as methyl, ethyl, n-propyl, isopropyl, n-butyl, isobutyl, sec-butyl or tert-butyl,
 a linear or branched alkenyl group containing from 2 to 6 carbon atoms and preferably from 2 to 4 carbon atoms, such as vinyl or allyl,
 a linear or branched alkoxy group containing from 1 to 6 carbon atoms and preferably from 1 to 4 carbon atoms, such as methoxy, ethoxy, n-propoxy, isopropoxy, n-butoxy, isobutoxy, sec-butoxy or tert-butoxy groups,
 a phenyl group,
 a halogen atom, preferably a fluorine, chlorine or bromine atom.

As regards the definition of x, x is advantageously equal to 0, 1 or 2 and more preferentially equal to 1.

The process of the invention preferably applies to the compounds corresponding to formula (I) in which R represents a hydrogen atom, an alkyl group containing from 1 to 4 carbon atoms and x is equal to 1 or also an alkoxy group containing from 1 to 4 carbon atoms and x is equal to 1.

As illustrations of compounds corresponding to formula (I), mention may be made of:
 those corresponding to formula (I) in which x is equal to 0, such as:
  phenol,
 those corresponding to formula (I) in which x is equal to 1, such as:
  pyrocatechol
  resorcinol
  o-cresol
  m-cresol
  2-ethylphenol
  3-ethylphenol
  2-propylphenol
  2-(sec-butyl)phenol
  2-(tert-butyl)phenol
  3-(tert-butyl)phenol
  2-methoxyphenol (guaiacol)
  3-methoxyphenol
  2-ethoxyphenol (guaethol)
  2-isopropoxyphenol
  salicylaldehyde
  methyl salicylate
  2-chlorophenol
  3-chlorophenol
  3-nitrophenol
 those corresponding to formula (I) in which x is equal to 2, such as:
  2,3-dimethylphenol
  2,5-dimethylphenol
  3,5-dimethylphenol
  2-hydroxy-5-acetamidobenzaldehyde
  2-hydroxy-5-ethamidobenzaldehyde
  2,3-dichlorophenol
  2,5-dichlorophenol
  3,5-dichlorophenol
  pyrogallol
 those corresponding to formula (I) in which x is equal to 3, such as:
  2,3,5-trimethylphenol
  3,5-di(tert-butyl)phenol
  2,3,5-trichlorophenol
 those corresponding to formula (I) bearing a naphthalene group, such as:
  1-naphthol
  2-naphthol
  1,2-dihydroxynaphthalene
  1,5-dihydroxynaphthalene
  2,3-dihydroxynaphthalene
  2,6-dihydroxynaphthalene
  2,7-dihydroxynaphthalene
  6-bromo-2-naphthol
 those corresponding to formula (I) bearing a sequence of benzene nuclei:
  2-phenoxyphenol
  3-phenoxyphenol Among the list of the abovementioned compounds, the aromatic compounds bearing at least one hydroxyl group used are preferentially: phenol, o-cresol, m-cresol, 3-ethylphenol, 2-tert-butylphenol, guaiacol or guaethol.

The hydroxylated aromatic compounds to which the separation process of the invention preferentially applies are guaiacol and guaethol, or a mixture thereof.

In accordance with the separation process of the invention, said mandelic compound present in said reaction medium resulting from said condensation reaction is preferentially an optionally substituted p-hydroxymandelic compound, whose formula, in acid form, is represented by formula (II) below:

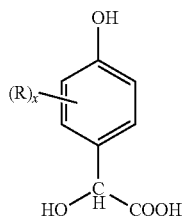

(II)

In said formula (II), R and x have the meaning given in formula (I).

According to the invention, said p-hydroxymandelic compound is present in said reaction medium in salified form, i.e. hydrogen atoms of the hydroxyl group and of the carboxylic group COOH of the mandelic compound represented by formula (II) are replaced with a metal cation, in particular an alkali metal cation.

The condensation reaction which results in the reaction mixture subjected to said separation process according to the invention is performed in water in the presence of at least one hydroxylated aromatic compound and glyoxylic acid, in the liquid phase, in the presence of an alkaline agent. As alkaline agents, use is preferably made of an alkali metal hydroxide which may especially be sodium or potassium hydroxide. For economic reasons, sodium hydroxide is preferentially chosen. The presence of the base leads to salification of the hydroxylated aromatic compound, on the one hand, and of the carboxylic function of glyoxylic acid, on the other hand. The alkali metal hydroxide solution used has a concentration generally between 10% and 50% by weight. The amount of alkali metal hydroxide introduced into the medium takes into account the amount required to salify the hydroxyl function of the hydroxylated aromatic compound and the carboxylic function of glyoxylic acid. Generally, the amount of alkali metal hydroxide ranges between 70% and 120% of the stoichiometric amount. Glyoxylic acid may be used as an aqueous solution with a concentration ranging, for example, between 15% and 99% by weight or may be used in hydrate form. Use is preferably made of commercial solutions whose concentration is about 50% by weight. Glyoxylic acid is reacted with at least one hydroxylated aromatic compound. The mole ratio between said hydroxylated aromatic compound and glyoxylic acid ranges between 1.0 and 4.0. A mixture of several hydroxylated aromatic compounds may be used. Advantageously, the condensation reaction is performed in the presence of a catalyst of dicarboxylic acid type as described in WO 99/65853. The amount of catalyst used, expressed by the ratio between the number of moles of catalyst and the number of moles of glyoxylic acid, is advantageously chosen between 0.5 and 2.5 and preferably between 1 and 2. The condensation reaction temperature is advantageously chosen between 0 and 100° C. and preferably between 10° C. and 80° C. The reaction is performed at atmospheric pressure, under air or under a controlled atmosphere of inert gases, preferably of nitrogen or optionally of rare gases, in particular argon. Nitrogen is preferentially chosen. The condensation reaction may be performed in different types of reactors, for example in a tubular reactor (plug-flow reactor) or alternatively in a cascade of stirred reactors.

The condensation reaction which results in the reaction mixture subjected to said separation process according to the invention is preferentially carried out by performing the reaction of glyoxylic acid with guaiacol or the reaction of glyoxylic acid with guaethol or alternatively the reaction of glyoxylic acid with guaiacol and guaethol. In the first two cases, the condensation reaction leads to the production of a p-hydroxymandelic compound substituted ortho to the hydroxyl group respectively with a methoxy group (condensation of glyoxylic acid with guaiacol) and with an ethoxy group (condensation of glyoxylic acid with guaethol), said p-hydroxymandelic compound being in salified form. In the third case, the condensation reaction of glyoxylic acid with guaiacol and guaethol leads to the coproduction of a salified p-hydroxymandelic compound substituted ortho to the hydroxyl group with a methoxy group and of a salified p-hydroxymandelic compound substituted ortho to the hydroxyl group with an ethoxy group.

In accordance with the separation process of the invention, said aqueous reaction medium subjected to said decantation step a) comprises at least said hydroxylated aromatic compound in salified form in excess and at least one mandelic compound, preferentially a p-hydroxymandelic compound, in salified form. Said reaction medium also generally comprises other mandelic compounds in salified form, in particular an o-hydroxymandelic compound and a hydroxylated dimandelic compound (two CHOH—COOM functions and one OM function, in which M is an alkali metal cation). Decantation of said reaction medium is facilitated since said reaction medium is constituted of an aqueous phase and of an organic phase that have a tendency to demix. The organic phase is essentially formed from the excess of said hydroxylated aromatic compound in non-salified form, whereas the aqueous phase is mainly formed from at least said p-hydroxymandelic compound in salified form and from an amount of the excess of said hydroxylated aromatic compound in salified form. Said organic phase represents not more than 20% by weight, preferably not more than 10% by weight and even more preferably not more than 7% by weight of said aqueous reaction medium and it is formed from at least 40% by weight, preferably at least 70% by weight of said hydroxylated aromatic compound in non-salified form. Said aqueous phase is formed from at least 1% by weight of said p-hydroxymandelic compound and from not more than 15% by weight of said hydroxylated aromatic compound in salified form.

Said reaction medium is aqueous and basic. The pH of said reaction medium, on conclusion of the condensation reaction, is preferentially between 10 and 12, generally in the region of 11, i.e. between 10.5 and 11.5.

Said decantation step is performed in a continuous, semi-continuous or batchwise operation. Preferably, the decantation is performed in a continuous operation.

Said decantation step is conducted at a temperature between 10 and 80° C. Preferably, it is conducted at the condensation reaction temperature. The duration of said decantation step is from a few minutes to a few hours, generally between 0.5 and 2 hours.

According to a preferred embodiment of the process of the invention, said organic phase obtained after decantation is recycled into the condensation reaction step, upstream of the separation process according to the invention. Decantation of the organic phase of said reaction medium according to said step a) of the separation process of the invention, upstream of said adsorption step b), makes it possible to perform direct recycling of a large amount of the excess of said hydroxylated aromatic compound present in said organic phase, without the need to subject said amount to the subsequent adsorption step. The result is a decrease in the amount of hydroxylated aromatic compound in salified form to be adsorbed onto said adsorbent support in step b) of the separation process of the invention and consequently reduced dimensioning of the adsorption apparatus. The implementation of the decantation makes it possible to recycle directly about 20% to 80% by weight and preferably from 40% to 60% by weight of the excess of said hydroxylated aromatic compound into the condensation reaction step.

In accordance with said step b) of the separation process according to the invention, said aqueous phase, derived from said decantation step, is placed in contact with an adsorbent support so as to separate said hydroxylated aromatic compound by adsorption. More precisely, said step b) is performed by placing the aqueous phase derived from said step a) and comprising at least an excess of said hydroxylated aromatic compound and at least said mandelic compound, preferentially at least said p-hydroxymandelic compound, in salified form, in contact with an adsorbent support, leading to the selective adsorption of said hydroxylated aromatic compound onto said support and the recovery of an aqueous stream comprising at least said p-hydroxymandelic compound. Preferably, said adsorbent support is chosen from active charcoals, adsorbent polymers, zeolites, molecular sieves and anion-exchange resins as described in patent application WO 2009/141280. An active charcoal based on coal, peat, lignite, oil distillation residues, or from any carbon-rich vegetable organic matter: wood, bark, twigs, wood pulp, fruit shells, preferably coconut shells or groundnut shells, is very preferentially chosen. The amount of adsorbent support used is determined as a function of the adsorption efficacy of the adsorbent support. A person skilled in the art will know how to adapt the amount of adsorbent to obtain total adsorption. The amount of adsorbent represents at least from 2 to 10 times the weight of the hydroxylated aromatic compound to be adsorbed. An excess of adsorbent is preferably used, for example an excess of 10% to 20% of the weight of calculated adsorbent. Preferably, said step b) is performed at a temperature of between 0 and 100° C., preferably between 15 and 80° C. and even more preferably at the temperature at which said step a) is performed.

The characteristics of the adsorbent support and the advantages of the technique of separation by adsorption/desorption are explained in patent applications WO 2011/039331 and WO 2009/141280, in particular the advantages reside in the absence of need to perform a neutralization step after the condensation step: said hydroxylated aromatic compound in salified form is selectively adsorbed onto said adsorbent and is then recovered before being recycled into said condensation step, upstream of the process of the invention.

Advantageously, said step b) of the separation process according to the invention is performed by placing said adsorbent support in a stirred reactor or in a column. It is preferentially performed co-currentwise: said aqueous phase and said basic solution have an identical direction of circulation, either descending or ascending, which is favorable for minimizing the amounts of water and of basic solution introduced for the phase of regeneration of said hydroxylated aromatic compound.

According to said step b) of the separation process according to the invention, an aqueous stream comprising at least one mandelic compound, preferentially at least one p-hydroxymandelic compound, in salified form, is recovered at the outlet of the adsorption device, generally a column, in which the adsorption takes place, whereas the hydroxylated aromatic compound is adsorbed on the support. Preferably, not only said p-hydroxymandelic compound but also an o-hydroxymandelic compound and a hydroxylated dimandelic compound are recovered in said aqueous stream.

The excess of said hydroxylated aromatic compound fixed onto the adsorbent is desorbed via a regeneration treatment, in particular via a heat treatment, a basic treatment or a basic aqueous treatment. The basic treatment is performed by using a base, for example sodium hydroxide or potassium hydroxide. A basic aqueous solution with a concentration of from 1% to 50% by weight is advantageously used. Sodium hydroxide is usually used. The amount of base used is at least equal to the amount of hydroxylated aromatic compound to be regenerated.

According to a preferred embodiment of the separation process of the invention, said hydroxylated aromatic compound, once desorbed, is recycled in salified form into the condensation reaction step, upstream of the separation process according to the invention. An advantage lies in the absence of need to perform neutralization of said hydroxylated aromatic compound in salified form before recycling since said condensation reaction uses a hydroxylated aromatic compound in salified form.

According to another preferred embodiment of the process of the invention, it is advantageous to perform a step of acidification of said reaction medium prior to said decantation step and/or to perform a step of acidification of said aqueous phase, derived from said decantation step, prior to said step of placing in contact with an adsorbent support. Advantageously, said acidification step prior to said decantation step is such that the amount of hydroxylated aromatic compound present in the aqueous phase is lowered by 10% to 70% by weight relative to the amount of said aromatic compound present in said aqueous phase when the reaction medium is not subjected to an acidification step. Thus, prior acidification of said reaction medium makes it possible to substantially increase the amount of hydroxylated aromatic compound directly recycled into the condensation reaction step and consequently to perform said adsorption step b) under optimized conditions since a larger amount of the aqueous phase, depleted in hydroxylated aromatic compound, may be treated before saturating the adsorption device, generally an adsorption column, and before performing regeneration. Implementing said acidification step prior to said decantation step makes it possible to recycle directly up to, or even beyond, 80% by weight of the excess of said hydroxylated aromatic compound into the condensation reaction step. Said acidification step prior to said decantation step may be performed via any method known to those skilled in the art, for example by using a strong acid, such as sulfuric acid, a weak acid such as acetic acid, formic acid or $CO_2$.

Very advantageously, said step of acidification of said aqueous phase, derived from said decantation step, prior to said step of placing in contact with an adsorbent support is such that the pH is lowered by 0.1 to 3 points. Preferably, the pH of said aqueous phase is between 8 and 11. The acidification is performed by adding strong acid or weak acid or alternatively by using $CO_2$. Advantageously, sulfuric acid is used as strong acid and formic acid, acetic acid or $CO_2$ is used as weak acid. Acidification of said aqueous phase derived from said step a) allows better adsorption of said hydroxylated aromatic compound in salified form. It is particularly advantageous to perform the acidification of said aqueous phase using formic acid or acetic acid or alternatively using $CO_2$ so as not to give rise to the production of salts, especially sulfate salts.

The $CO_2$, advantageously used in one and/or the other of said acidification steps, preferentially originates from the electro-electrodialysis or bipolar membrane electrodialysis step d) described below in the present description which gives rise to the production of $CO_2$. Use may also advantageously be made of $CO_2$ recycled from the effluents produced downstream of the hydroxyaromatic aldehyde preparation process described below in the present description.

The separation process according to the invention may be performed in continuous mode (using the simulated moving bed (SMB) technology), in semi-continuous mode (column carousel) or in batch mode.

Said mandelic compound(s) obtained on conclusion of said step b) of the separation process according to the invention, preferentially said p-hydroxymandelic compound and generally also an o-hydroxymandelic compound and a hydroxylated dimandelic compound, are particularly advantageous since they are intermediate products that make it possible, inter alia, to obtain hydroxyarylacetic acids by reduction, or hydroxyarylglyoxylic (=hydroxyaryl α-oxoacetic) acids or hydroxyaromatic aldehydes by oxidation.

A preferred application of the separation process according to the invention is the preparation of hydroxyaromatic aldehyde, by oxidation of mandelic compound, in particular of mandelic compound of formula (II) in salified form, obtained on conclusion of said step b) of the separation process according to the invention.

Another subject of the present invention is a process for preparing hydroxyaromatic aldehyde from corresponding mandelic compound, comprising at least the following steps:
c) an oxidation reaction of at least said mandelic compound, obtained according to the separation process described above, to at least one alkoxybenzaldehyde hydroxylate compound,
d) transformation of at least said alkoxybenzaldehyde hydroxylate compound into hydroxyaromatic aldehyde.

In particular, the invention relates to a process for preparing hydroxyaromatic aldehyde using an aqueous reaction medium resulting from the condensation reaction, in water, of at least one aromatic compound bearing at least one hydroxyl group and in which the para position is free with glyoxylic acid in basic medium, said process comprising at least the following steps:
a) decantation of said reaction medium so as to recover an organic phase essentially comprising the excess of said aromatic compound and an aqueous phase formed from at least said mandelic compound and an amount of the excess of said aromatic compound;
b) placing said aqueous phase in contact with an adsorbent support, leading to selective adsorption of said aromatic compound on said support and to the recovery of an aqueous stream comprising at least said mandelic compound in salified form;
c) an oxidation reaction of at least said mandelic compound to at least one alkoxybenzaldehyde hydroxylate compound;
d) transformation of at least said alkoxybenzaldehyde hydroxylate compound into hydroxyaromatic aldehyde.

The invention also relates to a process for preparing hydroxyaromatic aldehyde using at least one aromatic compound bearing at least one hydroxyl group and in which the para position is free, said process comprising at least the following steps:
a condensation reaction, in water, of said aromatic compound with glyoxylic acid in basic medium, and recovery of the resulting aqueous reaction medium comprising at least one mandelic compound in salified form;
decantation of the reaction medium so as to recover an organic phase essentially comprising the excess of said aromatic compound and an aqueous phase formed from at least said mandelic compound and an amount of the excess of said aromatic compound;
placing said aqueous phase in contact with an adsorbent support, leading to selective adsorption of said aromatic compound on said support and to the recovery of an aqueous stream comprising at least said mandelic compound in salified form;
an oxidation reaction of at least said mandelic compound to at least one alkoxybenzaldehyde hydroxylate compound;
transformation of at least said alkoxybenzaldehyde hydroxylate compound into hydroxyaromatic aldehyde.

The oxidation reaction employed for carrying out said step c) of the process for preparing a hydroxyaromatic aldehyde according to the invention is advantageously performed in the presence of oxygen or air. Said oxidation reaction is performed at atmospheric pressure or under pressure. It is preferentially performed in basic medium, generally by adding an alkaline or alkaline-earth metal agent. Said oxidation reaction is generally performed in the presence of water as solvent. It is conducted at a temperature preferentially between 10 and 200° C. Said oxidation reaction is preferentially catalyzed, either by homogeneous catalysis or by heterogeneous catalysis. A catalyst of this oxidation reaction may be selected from catalysts comprising at least one metal element selected from the group formed by copper, nickel, cobalt, iron, manganese, and any mixture thereof. A preferred embodiment of said oxidation reaction consists in reacting at least one mandelic compound in salified form, derived from said step b) of the separation process according to the invention described above, with the oxidizing agent (oxygen or air), in the presence of at least one oxidation catalyst. Said oxidation step may be conducted in continuous or batch mode.

The reaction medium obtained on conclusion of said oxidation reaction is a basic aqueous medium in which the counterion of said alkoxybenzaldehyde hydroxylate is preferentially an alkali metal cation, preferentially sodium or potassium, or an alkaline-earth metal cation. It may also be an ammonium cation.

Said oxidation reaction affects the mandelic function in salified form, which is converted into an aldehyde function. Said mandelic compound(s), obtained according to the separation process described above, is (are) oxidized to alkoxybenzaldehyde hydroxylate compound(s). The term "oxidation" is understood here as an oxidative decarboxylation insofar as it comprises the departure of a carbon/late group, for example forming carbon dioxide.

Advantageously, said mandelic compound in salified form, subjected to said oxidation reaction, is a p-hydroxymandelic acid salt, a 4-hydroxy-3-methoxymandelic acid salt, a 3-ethoxy-4-hydroxymandelic acid salt or a 4-hydroxy-3-isopropoxymandelic acid salt so as to obtain the corresponding alkoxybenzaldehyde hydroxylate. It may also be a mixture of 4-hydroxy-3-methoxymandelic and 3-ethoxy-4-hydroxymandelic acid salts to obtain, after oxidation, the corresponding alkoxybenzaldehyde hydroxylates. Said 4-hydroxy-3-methonimandelic acid salt corresponds to the vanillate salt, a vanillin precursor, which is then obtained after performing said step d) of the hydroxyaromatic aldehyde preparation process according to the invention, and said 3-ethoxy-4-hydroxymandelic acid salt corresponds to the ethylvanillate salt, a precursor of ethylvanillin, which is then obtained after performing said step d) of the hydroxyaromatic aldehyde preparation process according to the invention.

In accordance with said step d) of the hydroxyaromatic aldehyde preparation process according to the invention, at least said alkoxybenzaldehyde hydroxylate compound is converted into hydroxyaromatic aldehyde.

According to a preferred embodiment of the hydroxyaromatic aldehyde preparation process according to the invention, said step d) is performed by electrodialysis. According to said embodiment, it consists in neutralizing at least said alkoxybenzaldehyde hydroxylated compound to hydroxyaromatic aldehyde by means of the electrodialysis technique. Said step d) consists in converting by neutralization at least said alkoxybenzaldehyde hydroxylate compound into hydroxyaromatic aldehyde and in producing a saline hydroxide solution, preferentially a sodium hydroxide solution. Advantageously, said step d) is performed either by electro-electrodialysis, also known as membrane electrolysis, or by bipolar membrane electrodialysis.

Implementation via electro-electrodialysis is performed using cation-exchange membranes. Neutralization of at least said alkoxybenzaldehyde hydroxylase compound to hydroxyaromatic aldehyde is performed by generating protons $H^+$ which gradually replace the cations (generally $Na^+$ ions) present in the aqueous reaction medium derived from said oxidation reaction, said cations migrating, under the effect of an electric field, in the direction of the cathode, across a cation-exchange membrane (known as a cationic membrane) to combine with the $OH^-$ ions produced by cathodic reduction of water and thus generating a cation hydroxide solution, preferentially a sodium hydroxide solution. The cation-exchange membranes (CEM) comprise strong acid groups, preferentially sulfonate groups, or weak acid groups, preferentially carboxylate groups. The cationic membranes used for performing the membrane electrolysis technique are chosen from heterogeneous membranes and homogeneous membranes. Heterogeneous membranes are prepared from cation-exchange resin particles incorporated into a phenolic resin or a polymer (polyvinyl chloride, polyethylene or the like). The assembly thus formed may coat a screen, for instance a polyester or polyacrylonitrile fabric. As heterogeneous cationic membranes advantageously used for performing the membrane electrolysis technique, mention may be made of the Ralex membranes sold by the company MEGA.

The homogeneous membranes are obtained by introducing a functional group onto an inert support, by chemical or radiochemical grafting. The chemical method, which is the one most commonly used, generally consists in functionalizing a latex of a polymer comprising aromatic nuclei, such as styrene/divinylbenzene or styrene/butadiene. The latex thus functionalized then serves to coat a screen as for the heterogeneous membranes. As homogeneous cationic membranes advantageously used for performing the membrane electrolysis technique, mention may be made of the Selemion membranes sold by Asahi Glass or the Neosepta membranes sold by Astom.

Advantageously and according to the electro-electrodialysis technique, said step d) consists in converting at least said alkoxybenzaldehyde hydroxylate compound into hydroxyaromatic aldehyde and in producing a hydroxide solution, preferentially a sodium hydroxide solution. Said step d), performed via the electro-electrodialysis technique, is conducted using a two-compartment electrolyzer. Figure 1 is a schematic representation of the functioning of such an electrolyzer in the case where it is a matter of converting sodium vanillate ((Na)VA) into vanillin (VA). It goes without saying that this representation is an example for facilitating the understanding of the functioning of the electro-electrodialysis technique, vanillate representing said alkoxybenzaldehyde hydroxylate compound and sodium representing said cations present in the aqueous reaction medium derived from said oxidation reaction.

According to the electro-electrodialysis technique, the $H^+$ and $OH^-$ ions are generated by the electrodes. In particular, according to the use of a two-compartment electrolyzer, the aqueous reaction medium to be treated, derived from said oxidation reaction step, is introduced into the "salt" compartment in which is found the anode on which the oxidation of water will take place, according to the reaction: $H_2O \rightarrow 2H^+ + \frac{1}{2}O_2 + 2e^-$. The $Na^+$ ions migrate in the direction of the cathode across a cation-exchange membrane and combine with the $OH^-$ ions produced by cathodic reduction of water, according to the reaction: $H_2O + e^- \rightarrow OH^- + \frac{1}{2}H_2$.

In one variant, a gas diffusion electrode may be used at the anode to oxidize the hydrogen generated according to the reaction: $H_2 \rightarrow 2H^+ + 2e^-$.

In another variant, a gas diffusion electrode may be used at the cathode to reduce oxygen according to the reaction $\frac{1}{2}O_2 + H_2O + e^- \rightarrow 2\ OH^-$.

It is even more advantageous, in order to protect the anode from the presence of organic compounds that may foul it or become oxidized thereon, to conduct said step d) using a three-compartment electrolyzer. In this configuration, an acid whose anion is not oxidizable, for example sulfuric acid, is circulated in the anode compartment. Figure 2 is a schematic representation of the functioning of such a three-compartment electrolyzer. The abbreviation CEM in Figure 2 means "cation-exchange membrane".

Irrespective of the type of configuration of the electrolyzer (two, three or more compartments), the $H^+$ and $OH^-$ ions are generated by the electrodes.

The temperature at which said step d) is performed when it is conducted by electro-electrodialysis is within the range that is compatible with cationic membranes. Advantageously, the temperature is between 15 and 90° C. The current density applied to the electrolyzer is preferentially between 1000 and 3000 A/m$^2$.

Implementation of said step d) by bipolar membrane electrodialysis is based on the generation of $H^+$ and $OH^-$ ions, not by the electrodes, but by means of said bipolar membrane (BM) itself. A bipolar membrane is constituted of three layers: a cation-exchange face, an anion-exchange face and a hydrophilic junction interface. Under the effect of an electric field, the solvation water at the membrane interface dissociates into $H^+$ and $OH^-$ ions, which migrate, respectively, toward the cathode, passing through the cationic face, and toward the anode, passing through the anionic face. As bipolar membranes advantageously used for performing the neutralization by electrodialysis, examples that may be mentioned include the one described in patent application WO 96/01286 or the membranes sold under the name Neosepta® by Astom or under the name Fumasep® by Fumatech. The bipolar membranes sold by the company MEGA may even more advantageously be used.

In a two-compartment configuration, the sodium vanillate solution is introduced into the "salt/acid" compartment. Under the action of the electric field, the $Na^+$ ions migrate to the cathode across a cation-exchange membrane and combine with the $OH^-$ ions originating from the anionic face of the bipolar membrane, to form sodium hydroxide in the base compartment. Simultaneously, the $H^+$ ions are produced on the cationic face of the bipolar membrane, leading to acidification (neutralization) of the vanillate solution.

In this configuration (Figure 3), a "salt/acid" compartment and a base compartment form an electrodialysis unit cell. An electrodialyzer comprises a stack of several unit cells, the number of which may advantageously range between 5 and 300.

Besides the membranes, the bipolar membrane electrodialyzer comprises at its ends an anode and a cathode which are, for example, composed of titanium coated with an electrocatalytic coating, 316L stainless steel or nickel. In the region of the electrodes, an electrolytic solution intended to ensure sufficient electrical conductivity is circulated: an anolyte at the anode; a catholyte at the cathode. A single electrolytic solution is often used. The electrolyte used may be a salt, an acid or a base, chosen from non-electroactive compounds. By way of example, mention may be made of neutral salts, such as sulfates, acids such as sulfuric acid or bases such as sodium hydroxide.

The current density applied to the bipolar membrane electrodialyzer is generally between 0.2 and 1.5 $kA/m^2$, preferably between 0.5 and 1.2 $kA/m^2$.

The temperature at which said step d) is performed when it is conducted by bipolar membrane electrodialysis is within a range that is compatible with the stability of the membranes. Advantageously, said step d) is conducted at a temperature between 15 and 90° C. According to a particular embodiment, said step d) is performed at a temperature between 45 and 90° C., preferably between 50 and 80° C. and even more preferably between 50 and 70° C. Any bipolar membrane that withstands this temperature is suitable for use. The bipolar membranes Neospepta®-BP1 and Neospepta®-HT are advantageously used for performing said step d). It is advantageous to work at a temperature above 45° C. because, besides the gain in electrical consumption due to the increase in electrical conductivity, operating in this higher temperature range makes it possible to use more concentrated solutions of alkoxybenzaldehyde hydroxylate, especially of sodium vanillate (the solubility of vanillin increasing greatly with the temperature).

The duration of implementation of said step d) conducted by bipolar membrane electrodialysis is preferentially less than one hour.

The electrolyzer or electrodialyzer used to perform said step d) may function in various ways. It may first function continuously by direct passage; several stages are then arranged in series to achieve the desired degree of conversion. It may function continuously with recirculation ("feed and bleed" mode); finally, it may function in batch mode; the solution recirculating until the desired degree of conversion or pH is obtained. In order to obtain good functioning of the electrolyzer or electrodialyzer, the electrical conductivity of the solutions must be sufficient. Since the conductivity of the salt/acid compartment decreases gradually as the conversion proceeds, it may be advantageous to adapt the current density to the degree of conversion, and to perform the conversion in two or even three stages functioning at decreasing current densities. In multi-stage functioning, the various stages may function in the same mode or in different modes. For example, when step d) is conducted in two stages, several embodiments are possible: the two stages may function continuously, the two stages may function in batch mode, the first stage may function continuously while the second stage may function in batch mode, or the first stage may function in batch mode while the second stage may function continuously.

In addition, in order for the functioning of the electrolyzer or electrodialyzer to be stable and efficient, pretreatment of the solutions used is possible. Pretreatment advantageously makes it possible to prevent fouling of the membranes. A person skilled in the art may especially choose a pretreatment from among the known techniques such as filtration, ultrafiltration, treatment on active charcoal and passage through chelating resins. The latter techniques, which are particularly preferred, make it possible to selectively remove the multivalent inorganic ions, in particular the $Ca^{2+}$, $Mg^{2+}$, $Ba^{2+}$, $Mn^{2+}$, $Zn^{2+}$, $Fe^{3+}$ and $Sr^{2+}$ ions. They also advantageously make it possible to fix soluble residues from the catalyst that might optionally be used during the oxidation step.

Acidification by electrodialysis, performed by electro-electrodialysis or bipolar membrane electrodialysis, is performed up to a pH value that allows the desired degree of conversion of the alkoxybenzaldehyde hydroxylate, especially of vanillate into vanillin. For example, in the preferred case in which it is desired to produce vanillin, since the pKa of the phenol function of vanillin is 7.50 at 25° C., a pH value of less than 6 will be chosen.

In accordance with the hydroxyaromatic aldehyde preparation process according to the invention, said saline hydroxide solution, preferentially said sodium hydroxide solution, produced during said step d) is advantageously recycled into said step c) to perform said oxidation reaction and/or into said step b) of the separation process described above and/or into said condensation reaction step upstream of said separation process described above.

In accordance with the hydroxyaromatic aldehyde preparation process according to the invention, said cation-exchange membranes, which are capable of ensuring the separation of the cations present in the basic aqueous medium derived from the oxidation reaction, and the bipolar membranes, which are capable of neutralizing said basic medium, allow neutralization of said alkoxybenzaldehyde hydroxylate compound to hydroxyaromatic aldehyde while at the same time considerably limiting the production of salts, in particular of sulfate salts (generally in the form of sodium sulfate salts), since the acidification of the basic medium derived from said oxidation step, performed by electrodialysis (electro-electrodialysis and bipolar membrane electrodialysis), does not require the use of an acid.

After performing said step d), the hydroxyaromatic aldehyde, preferentially vanillin and/or ethylvanillin, is in aqueous solution. It is then advantageously extracted with an organic solvent which dissolves the hydroxyaromatic aldehyde contained in the aqueous phase, said solvent being inert relative to the hydroxyaromatic aldehyde.

To isolate the hydroxyaromatic aldehyde, especially vanillin and/or ethylvanillin, from the extraction solvent, separation by recrystallization may be performed, but distillation is preferably performed, making it possible to obtain, for example as the distillation head fraction, the extraction solvent (if it is the most volatile compound of the mixture) and, for example as the distillation tail fraction, a hydroxyaromatic aldehyde, namely a mixture comprising essentially said hydroxyaromatic aldehyde, combined with heavy impurities called "tars" and with small amounts of light impurities. Reference is made for this stage in particular to the process described in the patent application WO 2010/007161.

Optionally, said hydroxyaromatic aldehyde may be treated in order to condition it in solid form. Preferably, it is purified by distillation followed by crystallization (by using one or more solvents or via the flaking technique). The resulting product may be optionally ground so as to obtain finer grains.

The effluents of the process according to the invention may be treated via the standard effluent treatment processes, as is described, for example, in international patent application WO 2013/135885.

According to one embodiment, an oxidation treatment may be performed. This oxidation treatment may require an oxidizing agent, which is preferably $H_2O_2$, but which may be another oxidizing agent such as oxygen, said oxidation treatment preferably being performed in the presence of UV. Said oxidation step is preferably performed via an advanced oxidation process (AOP) in the presence of $O_2$ and/or of $H_2O_2$ and of UV or a Fenton treatment comprising oxidation of the organic compounds in the presence of an oxidizing agent and optionally of iron(II) and/or iron(III).

According to another embodiment, the effluents may be subjected to a biotreatment by placing the aromatic organic compounds in contact with bacteria or enzymes that degrade said organic compounds. Among the bacteria and enzymes that may be used, mention may be made, in a non-exhaustive manner, of: *Pseudomonas putida, Pseudomonas mendocina, Pseudomonas putida, Comonas, Anthrobacter* sp., *Aspergillus niger*, mandelate dehydrogenase, benzoyl decarboxylase, vanillyl dehydrogenase, toluene monooxygenase, catechol-1,2-dioxygenase, catechol-2,3-dioxygenase, procatechuate-3,4-dioxygenase, procatechuate decarboxylase, etc.

According to another embodiment, the treatment of the effluents may comprise a step of adsorption of the aromatic organic compounds onto a substrate, for instance active charcoal, or alternatively one or more liquid-liquid extractions.

These variants may be combined.

However, since the effluents from the process according to the invention advantageously have a reduced or even zero content of sulfate salts, the effluent treatment process may be simplified. For example, the use of biotreatment alone is possible.

The invention will be explained in greater detail by means of the example below of a preferred embodiment of the invention, which is given in a nonlimiting manner.

EXAMPLE

In the example, the degree of conversion and the selectivity obtained are defined.

The degree of conversion (DC) corresponds to the ratio between the number of moles of reagent converted and the number of moles of reagent used.

The selectivity or the yield relative to the converted product (CY) is expressed by the ratio between the number of moles of product formed and the number of moles of reagent converted.

Condensation Reaction

The following are continuously charged into a first 150 mL 316L stainless-steel reactor equipped with a jacket, a mechanical stirrer, a pH electrode, a condenser system and an inert gas inlet:
- 1.14 kg/h of demineralized water
- 164 g/h (2.05 mol/h) of an aqueous solution of sodium hydroxide at 50% by weight
- 178 g/h (1.44 mol/h) of guaiacol (fresh and recycled).

This reaction mixture is maintained at a temperature of 35° C. This preparation is then fed into the first reactor of a system of 3 reactors in cascade, with an aqueous solution of glyoxylic acid at 50% by weight (107 g/h, i.e. 0.72 mol/h).

The 3 perfectly stirred reactors are made of 316L stainless steel and each have a volume of 1.5 L; they operate at 35° C.

The overall residence time is 2.1 hours.

At the outlet of the final reactor, a sample of this reaction medium is taken and the compounds present in the mixture are assayed by liquid chromatography.

The results obtained are as follows:
- conversion of guaiacol (GA): DC=47%
- disodium salt of 4-hydroxy-3-methoxymandelic acid (PMA(2Na)): CY(PMA(2Na)/GA)=86%
- disodium salt of 2-hydroxy-3-methoxymandelic acid (OMA(2Na)): CY(OMA(2Na)/GA)=6%
- trisodium salt of 2-hydroxy-3-methoxy-1,5-dimandelic acid (DMA(3Na)): CY(DMA(3Na)/GA)=8%

The reaction medium is sent to the decantation/neutralization/adsorption section to separate the excess sodium guaiacolate from the vanillyl-mandelic acid salts.

Decantation/Neutralization

The condensation outlet medium is transferred by pump at a delivery rate of 1.6 kg/h into a 1 L 316L stainless-steel reactor equipped with a mechanical stirrer, a pH electrode and a $CO_2$ inlet via a gas line immersed at the bottom of the reactor. The $CO_2$ delivery rate is regulated so that the pH of the reaction medium is neutralized at pH=10.5.

The reaction medium is then transferred into a 2L decanter equipped with a jacket and a temperature maintenance system, and in which the overall residence time is 1.2 hours. Decantation takes place at 35° C.

The decantation produces two streams:
- The organic layer, withdrawn from the bottom of the decanter, comprising guaiacol, at a delivery rate of 70 g/h. This stream is intended to be recycled directly into the condensation feed.
- The aqueous layer, the light phase, which contains the vanillyl-mandelic acid salts to be oxidized and 2.9% by weight of sodium guaiacolate.

To optimize the operating conditions of the absorption column, the aqueous phase is again neutralized to pH=10.0 in a 1 L 316L stainless-steel reactor equipped with a mechanical stirrer, a pH electrode and a $CO_2$ inlet via a gas line immersed at the bottom of the reactor. The $CO_2$ delivery rate is regulated so that the pH of the reaction medium is neutralized at pH=10.0.

Adsorption

The adsorption of the guaiacol is performed in a glass column equipped with a jacket and a system for maintaining the temperature at 35° C. The adsorbent used is Norit® C Gran active charcoal from the supplier Cabot Norit Activated Carbon: the bed of active charcoal in the column has a volume of 2.0 L.

The various steps of the cycle are controlled by a robot which starts and stops the various feed and collection pumps by interval timing. The time intervals were set beforehand to feed well-defined mass amounts depending on the steps.

The adsorption cycle comprises four steps:

Adsorption:

The decanted and neutralized condensation outlet medium feeds the top of the adsorption column via a peristaltic pump at a delivery rate of 3 L/h. At the column outlet, the stream is directed toward the storage buffer intended to feed the oxidation.

After feeding in 2.9 kg of condensation medium, the robot activates the second step of the cycle.

Start of the Regeneration Cycle:

The column is fed at the top with water and 10% sodium hydroxide via a peristaltic pump at a delivery rate of 3 L/h. At the bottom of the column, the outlet stream continues to be directed toward the oxidation reaction.

When 1.8 kg of water and then 10% of NaOH have been fed into the top of the column, the robot activates the third step of the cycle.

Regeneration:

The column is fed at the top with water via a peristaltic pump at a delivery rate of 3 L/h. At the bottom of the column, the outlet stream is directed toward the storage buffer intended for recycling of the sodium guaiacolate as an aqueous phase into the condensation.

After feeding 1.4 kg of water into the top of the column, the robot activates the fourth step of the cycle.

End of Cycle:

The column is fed at the top with the decanted and neutralized condensation outlet medium, via a peristaltic pump at a delivery rate of 3 L/h. At the bottom of the column, the stream is directed toward the storage intended for recycling of the sodium guaiacolate as an aqueous phase into the condensation.

When 1.0 kg of condensation medium has been fed into the top of the column, the robot activates the first step of the next cycle.

The delivery rate to the oxidation, averaged over the cycle, is 1.9 kg/h, whereas it is 1.0 kg/h for the sodium guaiacolate solution recycled into the condensation.

A sample is taken from each of the two column outlet drums and the compounds present in the mixture are assayed by liquid-phase chromatography.

The results obtained are as follows:

Oxidation Feed Medium:
Sodium guaiacolate (GANa): 1200 ppm
Disodium salt of PMA (PMA(2Na)): 7.0% by weight
Sodium Quaiacolate Recycled into the Condensation:
Sodium guaiacolate (GANa): 3.5% by weight
Disodium salt of PMA (PMA(2Na)): 0.2% by weight The degree of regeneration of the guaiacol adsorbed onto the column is 100%.

Oxidation Reaction

The 316L stainless-steel oxidation reactor equipped with a self-suction stirrer of cavitation type ("cavitator") or of Rushton type and with a jacket for efficient cooling is continuously fed with:

the mixture of the catalyst and of the aqueous solution of vanillyl-mandelic acid salts obtained from the adsorption column, i.e.:

1.95 kg/h of condensation reaction medium from which the excess sodium guaiacolate has been separated out (and then recycled) by adsorption on the active charcoal column. This mixture contains about 136 g/h of disodium salt of 4-hydroxy-3-methoxymandelic acid, 9 g/h of disodium salt of 2-hydroxy-3-methoxymandelic acid and 16 g/h of trisodium salt of 2-hydroxy-3-methoxy-1,5-dimandelic acid.

2 g/h of an aqueous solution of $CuSO_4$ in an amount expressed as molar percentage of metal relative to the molar sum of the vanillyl-mandelic acid salts: 0.04% each.

the appropriate amount of an aqueous solution of sodium hydroxide at 50% by weight corresponding at least to the amount required by the stoichiometry of the oxidation reaction.

the amount of oxygen at atmospheric pressure sufficient to have a virtually complete conversion of the vanillyl-mandelic acid salts. The oxidizing agent may be oxygen at atmospheric pressure or pressurized air.

This reaction takes place at 80° C.

At the outlet of the reactor, a sample of this reaction medium is taken and the compounds present in the mixture are assayed by liquid chromatography.

The results obtained are as follows:
conversion of the disodium salt of 4-hydroxy-3-methoxymandelic acid: DC>99.5%
yield of sodium vanillate VANa:
CY(VANa)/PMA=97%.

The solution is stored in a vat before being sent to the electrodialysis section.

Acidification of the sodium vanillate solution after oxidation is performed in batch mode in an electrodialysis pilot which is composed of an electrodialyzer, three hydraulic circuits respectively named electrolyte, salt/acid and base, each comprising a circulation pump and a floating flow meter (rotameter). The circuits are maintained at 53° C. by means of a hot water circulation, supplied by a thermostatically maintained bath, in internal coils. The electrodialyzer, which has a cross section of 0.02 $m^2$, comprises at each end a support onto which is attached each electrode (nickel anode and cathode), a membrane stack composed of two membranes with cationic ends of Neosepta C6610 type, seven bipolar membranes of Neosepta BP1 type stacked in successive layers alternating with seven Neosepta CMB cationic membranes.

2448 g of a sodium hydroxide solution at 1 mol/l and 2032 g of a sodium hydroxide solution at 0.5 mol/l are respectively introduced into the "electrolyte" and "base" circuits. In parallel, 2256 g of a sodium vanillate solution containing 4.1% of vanillin, 0.1% of ortho-vanillin, 0.6% of sodium hydroxide, 4% of sodium carbonate and 0.5% of vanillyl-mandelic acid are introduced into the "salt/acid" compartment. The pH and conductivity measurements are taken by probes dipping into this compartment. The pumps are switched on so as to ensure circulation of the various solutions (300 L/h for the electrolyte solution and 200 L/h for the "salt/acid" and "base" solutions) and homogenization of the temperature. The current generator is then switched on and the nominal intensity is set at 15 A by means of the potentiometer, i.e. a current density of 0.75 $kA/m^2$. The pH decrease is monitored over time. Transfer of sodium ions takes place from the "salt/acid" solution to the "base" solution. Substantial evolution of $CO_2$ is observed at and below a pH in the region of 8, requiring adjustment of the delivery rate of the "salt/acid" solution. When the pH reaches 5.3 (i.e. after about 50 minutes), the current generator and the circulation pumps are switched off. The solutions in the three compartments are emptied out, weighed and analyzed. The amounts recovered are, respectively, 2448 g of electrolyte solution, 2288 g of base solution and 1980 g of salt/acid solution. The coulombic yield obtained, corresponding to the ratio of the number of moles of elementary electrical charges really transferred to the amount of electrical charges which crossed the stack, is estimated at about 80%. The degree of conversion of the sodium vanillate into vanillin is greater than 95%. Said vanillin is then extracted into organic phase by adding a suitable solvent.

The invention claimed is:

1. A process for separating at least one mandelic compound in salified form from an aqueous reaction mixture resulting from condensation, in a basic aqueous medium, of at least one aromatic compound bearing at least one hydroxyl group and in which the para position is free with glyoxylic acid, said process comprising:
   a) decanting said reaction medium to recover an organic phase comprising aromatic compound in non-salified form and an aqueous phase comprising the at least one mandelic compound and an amount of the aromatic compound, each in salified form,
   b) contacting said aqueous phase with an adsorbent support to selectively adsorb aromatic compound from the aqueous phase on said support and recover an aqueous mixture comprising the at least one mandelic compound in salified form.

2. The process of claim 1, wherein said aromatic compound is selected from the group consisting of phenol and the hydroxylated aromatic compounds corresponding to formula (I):

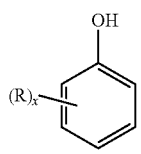

wherein:
   at least the position para to the hydroxyl group is free,
   R represents a hydrogen atom or one or more identical or different substituents,
   x, the number of substituents on a ring, is a number less than or equal to 4.

3. The process of claim 2, wherein said aromatic compound corresponds to formula (I), wherein R represents a hydrogen atom, an alkyl group containing from 1 to 4 carbon atoms, or an alkoxy group containing from 1 to 4 carbon atoms, and x is equal to 1.

4. The process of claim 1, wherein said aromatic compound is selected from the group consisting of phenol, o-cresol, m-cresol, 3-ethylphenol, 2-tert-butylphenol, guaiacol, and guaethol.

5. The process of claim 1, wherein said organic phase obtained after decantation is recycled into the condensation reaction.

6. The process of claim 1, wherein said step b) is performed co-currently.

7. The process of claim 1, wherein said aqueous stream obtained after said step b) comprises a p-hydroxymandelic compound, an o-hydroxymandelic compound, and a hydroxylated dimandelic compound.

8. The process of claim 1, further comprising desorbing said aromatic compound and recycling desorbed aromatic compound into said condensation reaction.

9. The process of claim 1, further comprising:
   acidifying said reaction mixture prior to the decanting step, and/or
   acidifying said aqueous phase prior to contacting the aqueous phase with the adsorbent support.

10. The process of claim 9, wherein acidification of said aqueous phase is effective to lower the pH of said aqueous phase 0.1 to 3 points.

11. The process of claim 9, wherein the acidification is performed by adding strong acid or weak acid or, alternatively, by using $CO_2$.

12. The process of claim 1, further comprising:
   c) oxidizing the at least one mandelic compound to at least one alkoxybenzaldehyde hydroxylate compound, and
   d) converting the at least one alkoxybenzaldehyde hydroxylate compound into at least one hydroxyaromatic aldehyde.

13. The process of claim 12, wherein said step d) comprises neutralizing the at least said alkoxybenzaldehyde hydroxylate compound into the hydroxyaromatic aldehyde and producing a saline hydroxide solution.

14. The process of claim 12, wherein the at least one mandelic compound is selected from the group consisting of p-hydroxymandelic acid salts, 4-hydroxy-3-methoxymandelic acid salts, 3-ethoxy-4-hydroxymandelic acid salts, 4-hydroxy-3-isopropoxymandelic acid salts, and a mixture of 4-hydroxy-3-methoxymandelic and 3-ethoxy-4-hydroxymandelic acid salts.

15. The process of claim 12, wherein said alkoxybenzaldehyde hydroxylate compound comprises a 4-hydroxy-3-methoxymandelic acid salt and the hydroxyaromatic aldehyde comprises vanillin.

16. The process as of claim 12, wherein said alkoxybenzaldehyde hydroxylate compound comprises a 3-ethoxy-4-hydroxymandelic acid salt and the hydroxyaromatic aldehyde comprises ethylvanillin.

17. The process of claim 12, wherein said step d) is performed by electro-electrodialysis using cation-exchange membranes.

18. The process of claim 12, wherein said step d) is performed by electrolyzing using a two-compartment electrolyzer or a three-compartment electrolyzer.

19. The process of claim 12, wherein said step d) is performed by bipolar membrane electrodialysis.

20. The process of claim 19, wherein said step d) is conducted at a temperature of between 45 and 90° C.

21. The process of claim 13, further comprising recycling said saline hydroxide solution into said step c), into said step b), and/or into said condensation reaction.

* * * * *